United States Patent [19]

Botich et al.

[11] Patent Number: 4,994,034
[45] Date of Patent: Feb. 19, 1991

[54] RETRACTABLE NEEDLE HYPODERMIC SYRINGE SYSTEM

[76] Inventors: Michael J. Botich, 1307 Hanover Ct., Ventura, Calif. 93003; Thor R. Halseth, 1223 Village Ct., Simi Valley, Calif. 93065

[21] Appl. No.: 378,275

[22] Filed: Jul. 11, 1989

[51] Int. Cl.⁵ .............................................. A61M 5/24
[52] U.S. Cl. ..................................... 604/110; 604/198
[58] Field of Search ............... 604/110, 192, 194, 197, 604/198, 213, 214, 220, 226

[56] References Cited

U.S. PATENT DOCUMENTS 3,046,985 7/1962 Saenz .................... 604/197
3,306,290 2/1967 Weltman ............. 604/197
4,747,831 1/1988 Kulli ................... 604/110

FOREIGN PATENT DOCUMENTS 8900435 1/1989 World Int. Prop. O. .......... 604/110

Primary Examiner—Stephen C. Pellegrino
Assistant Examiner—Corrine Maglione
Attorney, Agent, or Firm—Cislo & Thomas

[57] ABSTRACT

A hypodermic injection system with a retractable needle wherein the needle retracts within the interior cavity of a syringe plunger, so that the needle is safely and confinedly held within the plunger for ease of handling and transport, while remaining safely therein. A cylindrical spring housing has resilient fingers which can capture a coiled spring which biasly holds a needle holder against the retaining force of the resilient fingers. The plunger has a frangible end, which, when engaging the resilient fingers under a pre-determined amount of force, dissociate while remaining inwardly-tapered shoulders spread the resilient fingers, allowing the coiled spring to eject the needle and its holder into the interior cavity of the syringe plunger.

16 Claims, 2 Drawing Sheets

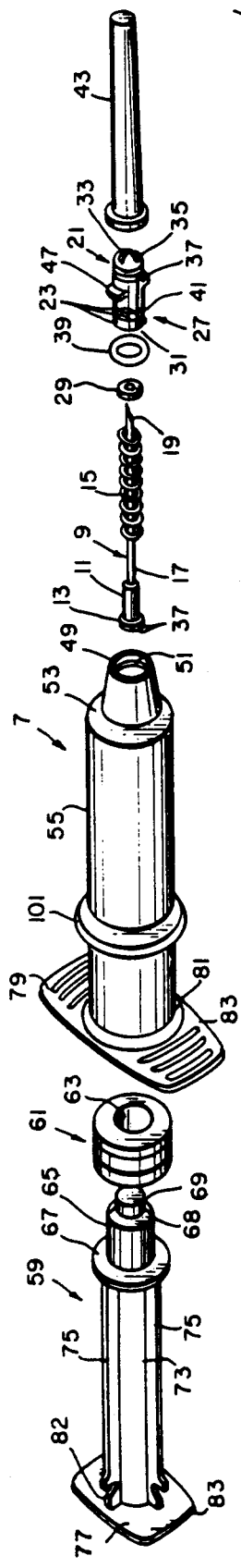
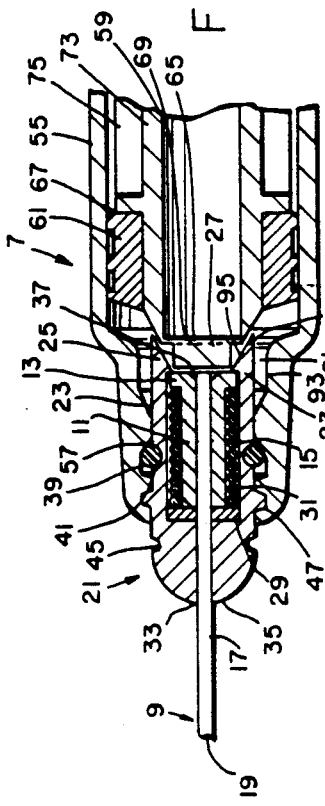
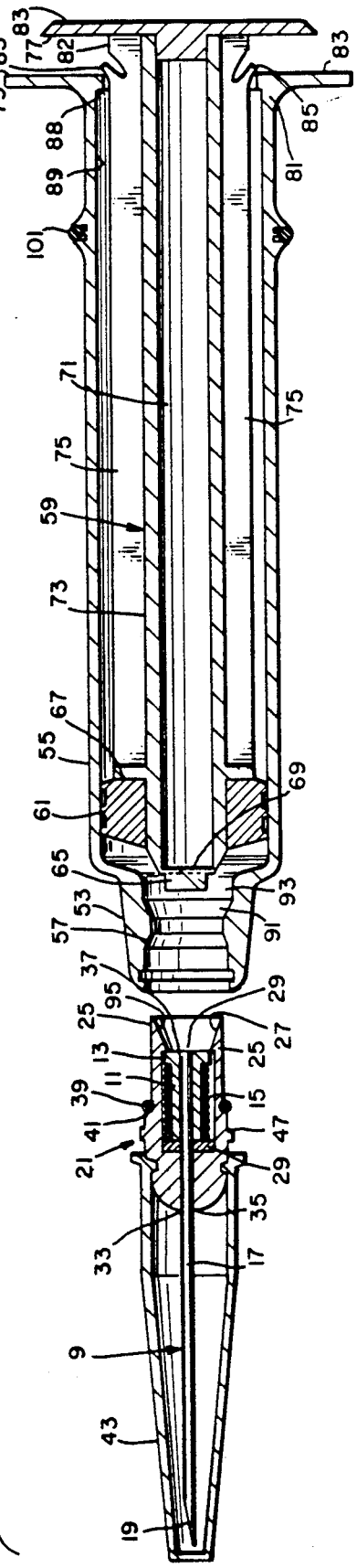

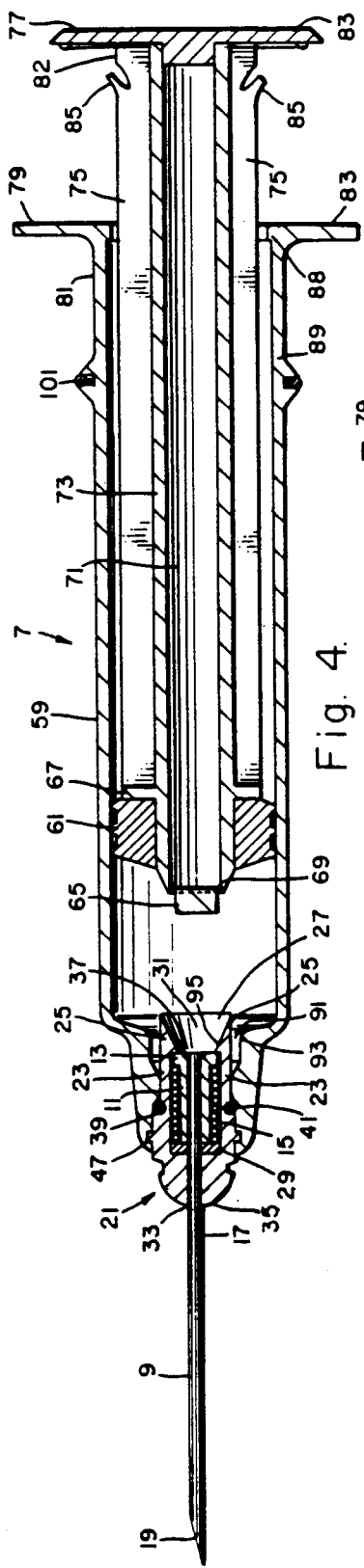

RETRACTABLE NEEDLE HYPODERMIC SYRINGE SYSTEM

BACKGROUND OF THE INVENTION

This invention relates generally to hypodermic needles, and particularly to hypodermic needles that are particularly suited for quickly and effectively removing the sharp injection needle which poses a serious health threat.

Various types of hypodermic needles currently exist in the art, with the object being to provide a protective cover or cap over the possibly wound-inflicting needle. Needles found in hypodermic syringes must be very sharp to quickly and easily puncture the skin of the patient in order to provide medicinals beneath the layer of skin. Additionally, the hypodermic needle is usually very thin and hard to see, especially in low-light conditions. Oftentimes, doctors and nurses accidentally prick themselves with the needle, either prior to or after an injection of a patient.

Pricking oneself prior to the injection of a solution does not present much of a health risk, since the needles to be used are usually sterilized. Also, hypodermic syringes usually come with a needle cap which is secured over the top of the needle to prevent the accidental puncturing of skin. When the doctor or nurse takes off the needle cap, exposing the needle, there is usually little risk of being injured by the needle. However, upon placing the needle cap back onto the needle, oftentimes the fingers can be pricked by a slight visual miscalculation or by a motorneuro mistake. The consequences of this type of accident are more extreme.

Since the needle has already punctured the skin of the patient, blood and body fluid along with the viruses or bacteria which may be found in the patient could possibly be transferred to the healthcare provider by a single accidental prick.

Various types of diseases previously known could be conveyed by such an accident, including hepatitis and cholera.

In the last decade, an even more menacing and lethal virus, the Acquired Immunity Deficiency Syndrome, or AIDS virus, is easily communicated by such an accidental and catastrophic event. Since there is no known cure for AIDS at this time, a great deal of care is required to prevent the accidental prick of the health care provider by a hypodermic needle which has previously been used on a patient.

Many types of syringes have been developed in an effort to address this problem yet allow the ease of use of more conventional hypodermic needles.

Many of those devices are herein described below:

U.S. Pat. No. 3,134,380 issued to T. Armao on May 26, 1964 discloses a hypodermic syringe needle having a shield which need not be removed prior to the use of the needle and which can be disposed of along with the needle itself. Holes are provided near the end of the shield to permit the escape of air as the shield is collapsed allowing the needle to protrude through the protective caps. The cap is held in an extended position by a spring which yields upon injection.

U.S. Pat. No. 3,890,971 issued to T. A. Leeson on June 24, 1975 discloses a safety syringe for one time use including a plunger which is lockable by detent members and slidably needle cap which is also permanently lockable to prevent reuse. The needle cap slides over the exterior of the syringe barrel and over the fixed needle.

U.S Pat. No. 4,367,738 issued to R. Legendre on Jan. 11, 1983 discloses a pre-filled syringe having spikes upon the plunger rods to prevent the withdrawal of the plunger from the syringe barrel. No means is disclosed for protecting the tip of the needle from accidental pricking.

U.S. Pat. No. 4,416,663 issued to R. N. Hall on Nov. 22, 1983 discloses a self sterilizing needle, wherein a capsule containing sterilizing fluid and having perforated ends of flexible material with elastic memory tendencies for self sealing after actual penetration by the forward end of the needle. The capsule is coaxially and slidably received over the forward end of the needle with the forward exposed end of the needle slidably penetrating one end of the capsule and perforation for sterilizing of the needle. A syringe is provided for axially urging and positioning the capsule outward to its original position of rest. Then, the exposed end of the needle is again enclosed in the capsule for sterilization when the hypodermic penetration force is removed.

U.S. Pat. No. 4,631,057 issued to C. B. Mitchell on Dec. 23, 1986 discloses a needle coupled to a syringe barrel, wherein a needle guard is mounted on the barrell for movement from a retracted position in which the guard does not shield the needle to an extended position in which the guard shields the needle.

U.S. Pat. No. 4,695,274 issued to R. L. Fox on Sept. 22, 1987 discloses a safety needle attachment wherein the needle is initially and entirely surrounded by a protecting jacket which is releasably interlocked with a holder. When the needle is to be used, an interlocker is released and the jacket is effectly telescoped over the holder to project the needle through a membrane over the end of the jacket to a working position.

U.S. Pat. No. 4,702,739 issued to N. M. Milorad on Oct. 27, 1987 discloses a hypodermic needle having a sleeve extending from a holder protectively covering the needle so that the sleeve can be placed against the body part where injection is to occur and with the needle tip end proximate the body part. By sliding the holder toward the body part a detent restraint holding the sleeve in an extended position is overcome and relative retraction movement effected therewith.

U.S. Pat. No. 4,731,068 issued to J. E. Hesse on March 15, 1988 discloses a non-reloadable syringe wherein the plunger is permitted to be withdrawn for purposes of loading the syringe and permitted to be urged forward to discharge the contents of the syringe. However, means is provided wherein subsequent retraction of the plunger assembly is inhibited to prevent further loading and use of the syringe.

U.S. Pat. No. 4,735,618 issued to J. Hagen on April 5, 1988 discloses a protective enclosure for a hypodermic syringe needle formed by a tubular sleeve sized for friction fitting engagement over the barrel portion of the syringe. A needle guard portion is located at an opposed end and pivotally removable arms operate to permit the needle to pass through a central channel of the needle guard.

U.S. Pat. No. 4,737,144 issued to P. V. Choksi issued April 12, 1988 discloses a syringe system comprising a tubular barrel and a sleeve mounted on the barrel to slide lengthwise from a retracted position in which the needle is exposed, and an extended position in which the sleeve extends protectively about the needle.

U.S. Pat. No. 4,737,150 issued to H. Baeumle on April 12, 1988 discloses a tube-cannula syringe, the first cannula being disposed so as to be displaced relative to the second cannula to be removable or displacable in the longitudinal direction of the syringe.

U.S. Pat. No. 4,738,663 issued to David E. Bogan on April 19, 1988 discloses a sleeve guide having a pair of fasteners with cavities formed in them that fit over the flange which are located on hypodermic syringes for grasping in the user's fingers. The guide in the retracted position prevents the accidental pricking by the needle.

U.S. Pat. No. 4,743,233 issued to Michael B. Schneider on May 10, 1988 discloses a slidable sleeve over a syringe barrel that is connectable in a first position extending over a hypodermic needle and that is reconnectable in a second position along the syringe barrel to expose the needle for use.

U.S. Pat. No. 4,747,829 issued to J. Jacob et al on May 31, 1988 discloses a pre-filled syringe with a retractable needle. A barrel of the syringe is removable within a casing from a remote pre-injection position to a forward injection position and back again. The barrel is moved forward allowing the needle to pass through an opening in a cap prior to injection.

U.S. Pat. No. 4,747,830 issued to W. W. Gloyer et al on May 31, 1988 discloses a syringe having a hollow barrel formed at the distal end to receive an injection piston carried by the plunger member which allows the needle to also to retract within the barrel by extracting the piston.

U.S. Pat. No. 4,752,290 issued to J. J. Schramm on June 21, 1988 discloses a tubular shield which is adapted to protect users from injury. The tubular shield cooperates with the raised surfaces on the body of the medical appliance to be protected.

U.S. Pat. No. 4,755,170 issued to T. A. Golden on July 5, 1988 discloses a protective sealing device comprising a block with which a sharp end of the needle can be held within to prevent accidental puncture. Also disclosed is a retaining shield which can be retracted over the needle to prevent accidental puncture.

U.S. Pat. No. 4,772,272 issued to B. C. McFarland on Sept. 20, 1988 discloses a protective sleeve for a hypodermic needle which sleeve is completely dissociable from the hypodermic syringe. The protective sleeve is moved over the needle protecting position to the needle injection position solely by axially movement of the protective sleeve.

It is desirable that the hypodermic needle can be made available in a safe condition prior to injection so that the health care provider will not accidentally prick his finger and require a new sterilized needle prior to the injection of the patient. It is also a requirement that after injection using the hypodermic needle, that the needle can be safely and easily discarded without representing a continued health risk to anyone who may encounter the hypodermic needle, either on the premises of the health care facility, or in transit or arrival at the refuse collection area or dump.

There is potentially a great interest in the health care industry to manufacture, sell, distribute and use a hypodermic needle that provides the type of safety as described above. It can be easily operated using one hand, proves to be completely reliable, and is easily and cheaply manufactured, yet still has a great deal of versatility for various applications using various needles in diameter and length.

The features described above as being desirable above for hypodermic syringes are all provided for by the present invention.

SUMMARY OF THE INVENTION

The present invention is embodied in an approved hypodermic syringe system which is entirely safe prior to injection due to a protective cover tip. Furthermore, after injection, the hypodermic syringe system is entirely safe, since the health care provider, using one hand, can retract the needle into an isolation container which can be easily and safely discarded, preventing the injury or transmission of any dangerous viruses or bacteria. In addition, the hypodermic syringe system is easily manufactured, easy to use, and provides visual and audible confirmation that the needle has been safely retracted after injection.

More particularly, the hypodermic injection system comprises a cylindrical syringe housing, holding a retractable injection needle which can be safely, quickly, and easily retracted within a specially designed syringe plunger. Furthermore, the plunger is fixedly held within a specially designed syringe barrel. The syringe barrel, plunger, and needle assembly can be easily discarded without the dangers associated with an exposed needle or needle that can be easily uncapped.

In more specific description of the invention, the injection needle has a sharp end, a shaft with an axial passageway therethrough, and a holder defining a raised lip. The injection needle is mounted within a cylindrical spring housing having resilient fingers which are spreadable radially outward on a first end and extending tabs extending radially outward on an external surface of the cylindrical spring housing to provide a mechanism for associating the cylindrical spring housing with the syringe barrel. The cylindrical spring housing includes a first sealing means for providing a seal between the cylindrical spring housing and the holder of the hypodermic injection needle. Also, a second sealing means for providing a seal between the cylindrical spring housing and the syringe barrel is used.

An opening in a second end of the cylindrical spring housing is sized to receive the shaft of the injection needle while retaining the holder when both are forwardly positioned within the cylindrical spring housing. The resilient fingers of the spring housing have radially inwardly positioned hooks sized to engage and hold the raised lip of the holder of the injection needle when the shaft of the injection needle is forwardly located within the cylindrical spring housing. The hooks have inwardly tapered shoulders so as to be easily spread by complementing and outwardly positioned tapered shoulders of the syringe plunger.

A coiled spring is positioned axially within the cylindrical spring housing between the holder and the second end of the cylindrical spring housing. The spring exerts an expansive force between the holder of the injection needle and the second end of the cylindrical spring housing, a force which is less than the retaining force exerted by the hooks of the resilient fingers, thereby retaining the injection needle within the cylindrical spring housing against the expansive force of the spring.

The syringe barrel includes slots and grooves sized and positioned to receive the extending tabs of the cylindrical spring housing and the second sealing means to provide an air-tight seal between the exterior of the cylindrical spring housing and an interior of the barrel.

The interior of the barrel is shaped sufficient to engage the cylindrical spring housing and allow the resilient legs to flex radially outward.

The syringe plunger is sized to be received concentrically within the syringe barrel and has a hollow, axially located chamber therein. The syringe plunger has a frangible end with the outwardly tapered shoulders adjacent to said chamber. The frangible end disassociates from the syringe plunger and is injected into the chamber when the outward tapered shoulders forcibly engage the inwardly tapered shoulders of the hooks of the resilient fingers, thereby spreading the resilient fingers outwardly and disengaging the hooks from the raised lip of the holder of injection needle. The frangible end dissociates under a pre-determined normal force between the holder of the injection needle and the frangible end. This allows the coiled spring to eject the syringe needle from the cylindrical spring housing into the chamber within the plunger.

The chamber located within the syringe plunger may be evacuated so that when the frangible end breaks and ejects with the needle into the chamber, any peripheral fluid is also drawn into the chamber and away from the cylindrical spring housing.

Furthermore, an inwardly-oriented lip on the exterior of the plunger is positioned so as to engage the complementing slot within the interior of the syringe barrel when the plunger is in a fully-depressed position to lock the plunger within the syringe barrel, preventing its removal and access to the retained needle therein.

The holder of the needle can have a bright color (such as red) so as to be visually distinctive within the transparent syringe barrel and syringe plunger, so that the health care provider can readily determine that the syringe is in a safe condition for transport or discard. The exterior of the syringe barrel can also be fitted with a color-coded sizing ring, which quickly and clearly identifies the size or capacity of the syringe system.

In an alternative embodiment, the needle ejecting mechanism can be held on the end of the syringe plunger. In that configuration, the needle is retained by a frangible needle holder associated with the ejection end of the syringe barrel. The hypodermic needle has a head which can be readily grabbed by a modified end of the syringe plunger. Depression on the syringe plunger dissociates the needle from the frangible needle holder. Further depression on the syringe plunger allows a needle retractor to pass by engaging detents, while a similar coiled spring ejects the needle retractor which is now engaging the needle, ejecting the needle into the interior chamber of the syringe plunger.

The hypodermic syringe system of the present invention provides for a retractable needle which is durable, disposable, easy to manufacture, prevents the accidental pricking after use, and provides for greater ease of handling the hypodermic needle after use, including the subsequent discarding of the device. The hypodermic needle is extremely simple in construction, yet completing effective in injecting fluid below the skin, subsequently becoming completely safe after the injection of the fluid while the health care provider need only use one hand to retract the needle, leaving his other hand free. Furthermore, his or her fingers may remain in their relative positions to retract the needle.

Other aspects and advantages of the present invention will be apparent from the following description of the preferred embodiments, taken in conjunction with the accompanying drawings, which illustrate, by way of example, the principals of the invention.

BRIEF DESCRIPTION OF THE DRAWINGS

FIG. 1 is an exploded view of the hypodermic needle of the present invention;

FIG. 2 is a partial cross-sectional view of the hypodermic syringe of the present invention, shown with its plunger proximate to the needle housing;

FIG. 3 is a cross-sectional view of the hypodermic syringe of the present invention, with the needle housing, needle, and needle cap shown exploded from the syringe barrel;

FIG. 4 is a cross-sectional view of the hypodermic syringe in the present invention shown with the syringe plunger in a partially depressed position within the syringe barrel;

FIG. 5 is a cross-sectional view of the hypodermic syringe of the present invention shown with the syringe plunger in a fully depressed position and the needle fully retracted; and FIG. 6 is a cross-sectional view of an alternative embodiment of the hypodermic syringe of the present invention.

DESCRIPTION OF THE PREFERRED EMBODIMENTS

As shown in the drawings FIGS. 1-6, wherein like numerals represent like elements throughout, the hypodermic syringe 7 is best shown in exploded view as FIG. 1. The main components of the syringe 7 are a standard injection needle 9 having a specially-mounted holder 11 including an enlarged lip 13, located posteriorly thereto. A coiled spring 15 rides a shaft 17 of the injection needle 9 with an axially located passageway 19 therethrough. A cylindrical spring housing 21 includes a plurality of radial spaced resilient fingers 23 which include inwardly engaging an inferiorly positioned hooks 25 on the posterior end 27 of the spring housing 21. A sealing means or washer 29 is sized to be received within an inner cavity 31 of the spring housing 21.

The injection needle 9, including the enlarged lip 13 of the holder 11 can be forwardly positioned within the inner cavity 31 of the cylindrical spring housing 21. A cross-shaped opening 33 in a forward end 35 of the spring housing 21 allows the shaft 17 of the injection needle 9 to extend through the cross-shaped opening 33. The enlarged lip 13 is engaged by the hooks 25 when forwardly positioned within the spring housing 21, causing the resilient fingers 23 and hooks 25 to flex around the enlarged lip 13 and engage a top surface 37 of the enlarged lip 13.

The washer 29 provides a secure seal between the shaft 17 of the injection needle 9 and the inner cavity 3 of the spring housing 21. Finally, a gasket or O-ring 39 engages a circumferential groove 41, located midway between the posterior end 27 of the spring housing 21 and the forward end 35 of the spring housing 21. This configuration can be more clearly shown in FIG. 2, and also in FIG. 3, partially exploded from the other components of the hypodermic syringe 7 of the present invention.

Also, shown in FIG. 3 is a needle cap 43, which engages a forwardly-positioned second circumferential groove 45 of the spring housing 21. The spring housing 21 has radially-extending bayonet tabs 47, which provide locking engagement within bayonet slots 49 and a bayonet groove 51, located within a tapered nose 53 of a syringe barrel 55. Engagement between the spring housing 21 and the tapered nose 53 of the syringe barrel 55 is easily accomplished by aligning the bayonet tabs 47 with the bayonet slots 49 and pushing the spring housing 21 through the bayonet slots 49 and then rotating the bayonet tabs 47 within the bayonet groove 51 to provide locking engagement therebetween. The bayonet tabs 47 may have slanted edges (not shown) on opposing sides and the bayonet groove may have raised surfaces (not shown) to allow the slanted edges to pass by the raised surface in one direction of rotation. This effectively locks the spring housing 21 to the tapered nose 53 of the syringe barrel 55 in a racket-like manner.

The first tapered inner wall 57 within the tapered nose 53 of the syringe barrel 55 provides sealing engagement between the spring housing 21 and the syringe barrel 55, due to the tight fit of the O-ring 39 between the spring housing 21 and the first tapered inner wall 57.

A plunger 59 is sized to be received within the syringe barrel 55 and engages a plunger piston 61 of a conventional type commonly used with syringe systems known in the art, except that a cylindrical cavity 71 extends therethrough, allowing a frangible end 65 to enter the cylindrical cavity 71 of the plunger piston 61. The plunger piston 61 is positioned over the associated frangible end 65 and is supported by a rim 67. The length of the plunger piston 61 is such that outwardly tapered shoulders 68 extend through and above the passageway 63 of the plunger piston 61, joining the frangible end 65. Between the outwardly tapered shoulders 68 and the frangible end 65 is a circumferential groove 69 of a defined thickness of approximately 1/32 of an inch, which allows the frangible end 65 to dissociate from the outwardly tapered shoulders 68 upon a normal force on the frangible end 65 of approximately two pounds or less in the preferred embodiment. The circumferential groove 69 can, of course, simply be a thinner construction of material allowing frangibility.

The plunger 59 includes the cylindrical central cavity 71 running axially through the plunger 59 and adjacent to the frangible end 65. The cylindrical cavity 71 has a diameter sufficient to allow the enlarged lip 13 and the holder 11 and the associated shaft 17 of the injection needle 9 to be injected into the cylindrical cavity 71 and need not be circular. Furthermore, the cylindrical cavity 71 can be evacuated so as to allow the vacuuming effect upon the dissociation of the frangible end 65 from the outwardly tapered shoulder 68.

A plunger sleeve 73 defines the cylindrical cavity 71 while reinforcement ribs 75 provide support to the plunger sleeve 73 and are associated with the rim 67 to provide additional support when the plunger 59 is being depressed. A pushing plate 77 is located on a posterior end 82 of the plunger 59. The pushing plate 77 is sized sufficient to allow the thumb of a normal person to properly depress the plunger 59 when associated with the syringe barrel 55.

Also, finger retaining lips 79 are associated with the posterior end 81 of the syringe barrel 55 so as to allow the index finger and middle finger to grasp the finger-retaining lips 79 of the syringe barrel 55 while the thumb presses upon the pushing plate 77. Grooves 83 or knurling may be etched within the finger-retaining lips 79 or upon the pushing plate 77 to provide a greater coefficient of friction between the fingers and thumb and the finger retaining lip 79 and pushing plate 77, respectively.

Radially extending ratchet teeth 85 interrupt the reinforcing ribs 75 and are posteriorly located while being posteriorly flared to allow the ratchet teeth 85 to pass by an extending ratchet lip 88 defined by an interior wall 89 of the syringe barrel 55. Upon full depression of the syringe plunger 59 within the syringe barrel 55, the ratchet teeth 85 pass by the ratchet lip 88. The ratchet teeth 85 flexibly pass by the ratchet lip 88 and prevent the extraction of the plunger 59 from the syringe barrel 55.

In operation, the syringe 7 of the instant invention, functions very much like a conventionally known hypodermic syringe as found in the prior art. However, after injection of the substance to be injected, the hypodermic syringe 7 of the instant invention allows the dissociation of the frangible end 65 from the outwardly tapered shoulders 68 of the plunger 59 and the radial flexing of the resilient fingers 23 so that the hooks 25 release the enlarged lip 13 of the holder 11 of the injection needle 9.

Since a circumferential space 91 exists between the resilient fingers 23, and the inner wall 93 of the syringe barrel 55, the resilient fingers 23 can flex, releasing the holder 11. The resilient fingers will only flex when inwardly tapered surfaces 95 of the hooks 25 are engaged by the outwardly tapered shoulders 68 of the plunger 59. Such engagement takes place when the plunger 59 is pushed through the syringe barrel 55 and the frangible end 65 abuts against the top surface 37 of the holder 11. A normal force of less than 2 pounds exerted between the top surface 37 of the holder 11 and the frangible end 65 causes the frangible end 65 to dissociate from the outwardly tapered shoulders 68 of the plunger 59.

With the resilient fingers 23 flexed radially outward, causing the hooks 25 to release the holder 11, the compressed spring 15 exerts an ejecting force against the enlarged lip 13 of the holder 11, propelling the injection needle 9 along with the holder 11, as well as the dissociated frangible end 65 into the cylindrical cavity 71 of the plunger 59.

The above operation makes a very distinctive click sound alerting the health care provider that the device is now safe.

Also, if the cylindrical cavity 71 is evacuated, a suction pulls any residual fluids into the cylindrical cavity 71. Upon further depression of the syringe plunger 59 into the syringe barrel 55, the ratchet teeth 85 engage the ratchet lip 88, preventing the plunger 59 from being extracted from the syringe barrel 55.

The holder 11 can be a bright red or fluorescent color, while the plunger 59 and syringe barrel 55 can be manufactured from a transparent or translucent material so that the retracted position is readily identified in low light conditions and the needle is visibly safe for further handling, transport or discard.

Also, an interchangeable identification ring 101 can be positioned around the syringe barrel 55 so as to identify the hypodermic syringe 7 for whatever purpose.

The plunger 59, syringe barrel 55, holder 11, spring housing 21, and needle cap 43 can be made from a transparent or translucent plastic material. However, the spring housing 21 does not necessarily have to be transparent nor does the holder 11. Such materials and their manufacturer are well known in the art and will not be further herein described. The plunger piston 61 can be formed of a neoprene material sufficient to provide a seal between the plunger piston 61 and the syringe barrel 55 and is also commonly known in the art and will not be hereinafter described in more detail. The shaft 17 of the injection needle 9 is of material known in the art as well.

The O-ring 39 can be of a elastomeric material, just as the washer 29 may also be of a resilient material, so as to provide a proper sealing effect well known in the art. It should be noted that the spring housing 21 must be formed of a durable plastic material which is resilient, so that the resilient fingers 23 properly and radially outwardly extend in association with the syringe plunger 59. The syringe plunger must be of a more resilient or brittle material or have a proper thickness so as not to flex inwardly when the frangible end 65 dissociates from the plunger 59. It is important that the plunger 59 remains durable sufficient to cause the resilient fingers 23 to move radially outward when the inwardly tapered surfaces 95 of the hooks 25 engage the outwardly tapered shoulders 68 of the syringe plunger 59. Specific examples of types of plastics and thicknesses are not required, as these can be readily determined by those ordinarily skilled in the art of plastics manufacture.

In an alternative embodiment, the mechanism responsible for ejecting the injection needle 9 can be fully positioned within the syringe plunger 59. As shown in FIG. 6, some slight variations in structure are necessary to achieve similar if not identical results as described in the first embodiment of the invention.

The injection needle 9 is held within a frangible needle holder 105, which includes a frangible cone 107, which engages an enlarged section 109 of the injection needle 9. The injection needle 9 has a length sufficient to extend well within the syringe barrel 59 and has an extraction end 111, which can be engaged by extraction hooks 113 of similar design as shown in FIGS. 1-5.

A needle retractor housing 115 is located and held on an inward end 117 of the syringe plunger 59, specifically held in place by detents 117, defined within the interior wall 119 of the cylindrical cavity 71 of the plunger 59. The compressed spring 17 exerts a force between the needle retracting housing 115 and the inner end 116 of the plunger 59. The force exerted by the spring is not sufficient to force the needle retractor housing 115 past the detents 117.

In operation the plunger 59 is pushed into the barrel 55 having outwardly tapered shoulders 121, which break the frangible cone 107, thereby releasing the enlarged section 109 of the injection needle 9. Further downward pressure on the plunger 59 forces the needle retractor housing 115 past detents 117, allowing the spring 15 to expand, pushing the needle retractor housing 115 deep within the cylindrical cavity 71 and taking with it the injection needle 9, because the hooks 113 grab the extraction end 111 as the needle retractor housing 115 is moved deeper into the cylindrical cavity 71 of the plunger 59. It should be noted that an extra piston spacer 123 is required for proper operation, due to the injection needle 9 extending within the syringe barrel 55.

Besides the above-identified differences, the second embodiment of the invention functions substantially as the first and the materials necessary for each of the components are similar to those materials as described in the first embodiment of the invention.

It should be appreciated from the foregoing description that the present invention describes an improved hypodermic needle with a retractable needle which is simple in construction, yet completely effective in retracting a needle once the needle has served its purpose in the injection of fluids below the surface of the skin. The hypodermic syringe of the present invention can be conveniently assembled from a minimum number of separate parts, all of which can be manufactured with relatively inexact precision, all of which are configured to facilitate compact and efficient operation. The hypodermic syringe of the present invention can be fully and safely operated by the use of one hand to retract the needle and allow for safe handling, transport, and discard.

Although the present invention has been described in detail with reference only to the presently-preferred embodiment, it will be appreciated by those of ordinary skill in the art that various modifications can be made without departing from the invention. Accordingly, the invention is limited only by the following claims.

We claim:

1. A hypodermic syringe system, comprising:
(a) a syringe barrel;
(b) a syringe plunger including a frangible end sealing an interior cavity, said syringe plunger sized to be received within and slide through said syringe barrel;
(c) an injection needle; and
(d) a spring holding means associated with and held by said syringe barrel, for holding said injection needle and selectively retracting said injection needle into said interior cavity of said syringe plunger when said syringe plunger abuts against and moves beyond a portion of said syringe barrel, causing breakage of said frangible end, and allowing said frangible end of said syringe plunger to separate, wherein said spring holding means, comprising: a holder for holding said injection needle; and a spring means for exerting an expansive force between said holder and said spring holding means, wherein said spring holding means selectively holds said holder and said spring means therebetween while allowing said injection needle to extend through said spring holding means in an assembled condition wherein said holder has a lip, said spring holding means has extending resilient fingers with interior and inferiorly positioned hooks to retain said lip of said holder in an assembled condition wherein, said frangible end of said syringe plunger has an engaging and complementing surface which abuts up against said hooks of said extending resilient fingers, spreading said extending resilient fingers radially outwardly to release said lip against the expansive force of said spring means when said syringe plunger moves beyond said portion of said syringe barrel.

2. A hypodermic syringe system as claimed in claim 1, wherein said frangible end of said syringe plunger separates when a predetermined normal force is exerted between said frangible end of said syringe plunger and said holder.

3. A hypodermic syringe system, as claimed in claim 2, wherein said frangible end of said syringe plunger spreads said extending resilient fingers radially outward upon depression of said syringe plunger past said predetermined point within said syringe barrel prior to exertion of said predetermined normal force, allowing said frangible end to dissociate and said spring means to propel said holder and injection needle into said interior cavity of said syringe plunger.

4. A hypodermic syringe system, as claimed in claim 3, wherein said spring holding means operatively dissociates from a nose section of said syringe barrel.

5. A hypodermic syringe system as claimed in claim 4, wherein said interior cavity of said syringe plunger is evacuated prior to the separation of said frangible end from said syringe plunger.

6. A hypodermic syringe system as claimed in claim 5, further comprising ratchet means for engaging said syringe plunger with said syringe barrel, preventing separation of said syringe plunger from said syringe barrel after said syringer plunger is depressed within said syringe barrel.

7. A hypodermic syringe system as claimed in claim 6, wherein said spring holding means includes at least one extending tab and wherein said nose section of said syringe barrel includes at least one interior axial slot and an adjoining inner radial slot, both sized to receive said tab and allow secure engagement between said spring holding means when associated with said nose section by positioning said tab through said axial slot and rotating said tab within said radial slot, thereby securing said spring holding means to said nose section.

8. A hypodermic syringe as claimed in claim 7, wherein said spring holding means has a frustoconical head, an axial bore through said head, of a sufficient diameter to receive said injection needle therethrough, and a cylindrical exterior groove sized to receive and retain an O-ring of sufficient size to engage tapered interior walls of said nose section of said syringe barrel and provide sealing engagement between said spring holding means and said nose section.

9. A syringe system as claimed in claim 8, wherein said holder is a highly visible color and wherein said syringe plunger and said syringe are made of a translucent or transparent material, to allow viewing said holder when ejected into said syringe through said syringe barrel.

10. A syringe system as claimed in claim 9, wherein said head of said spring holding means includes an engagement groove for engagement with a needle cap.

11. A syringe system as claimed in claim 10, comprising a color-coded ring of sufficient diameter to slide over an exterior surface of said syringe barrel and be retained thereby to identify the syringe system.

12. A hypodermic syringe, comprising a spring-loaded needle means for holding and ejecting a captured needle, barrel means for holding injectable fluid therein and connectable to said spring-loaded needle means on one end, and a hollow plunger means positionable within and movable through said barrel means, said plunger means having a breakable end which breaks free from one end of said hollow plunger means and allows said captured needle to be ejected into said hollow plunger means within said barrel means, wherein said spring loaded needle means having a housing with resilient fingers on one end, which can be spread radially outwardly by said one end of said hollow plunger means in contact therewith to release said captured needle from said housing, wherein said breakable end of said hollow plunger means breaks allowing said captured needle to be propelled out of said housing and into said hollow plunger means and be retained therein, wherein said breakable end of said hollow plunger means includes tapered shoulders which engage oppositely and complementing shoulders of said resilient fingers, allowing forward movement of said hollow plunger means to spread said resilient fingers radially outward, said syringe further comprising an extending tab and a receiving slot associated between an exterior of said hollow plunger means and the interior of said barrel means, said extending tab and said receiving slot oriented to lock together when said tab and said slot are brought into alignment with each other within said barrel means, thereby locking said hollow plunger means within said barrel means, wherein said spring loaded needle means operatively dissociates from said barrel means.

13. A hypodermic syringe as claimed in claim 12, wherein said hollow plunger means and said barrel means are substantially transparent, said captured needle having a distinctive appearance to be readily seen through said syringe plunger and said barrel means once ejected into said hollow plunger means.

14. A hypodermic syringe as claimed in claim 13, wherein said hollow plunger means includes an evacuated chamber to extract fluid from said spring loaded needle means upon the dissociation of said breakable end of said hollow plunger means.

15. A hypodermic injection system, comprising:
(a) an injection needle having a shaft with an axial passageway therethrough, said shaft having a sharp end and a holder defining a raised lip on another end;
(b) a cylindrical spring housing having an exterior surface, and resilient legs spreadable radially outward on a first end, said cylindrical spring housing having exteriorly located attachment tabs extending radially outward, a first sealing means for providing a seal between said cylindrical spring housing and said shaft of said injection needle, an opening on a second end of said cylindrical spring housing to receive said shaft of said injection needle while retaining said holder, said resilient legs having radially inwardly positioned hooks sized to engage and hold said raised lip of said holder of said injection needle when said shaft of said injection needle is forwardly positioned within said cylindrical spring housing, said hooks having inwardly tapered shoulders;
(c) a coiled spring means positioned axially within said cylindrical spring housing between said holder and said second end of said cylindrical spring housing, said spring means exerting a repulsive force between said holder of said injection needle and said second end of said cylindrical spring housing less than the retaining force exerted by said hooks of said resilient legs, thereby retaining said injection needle within said cylindrical spring housing against said repulsive force of said spring means;
(d) barrel means for engaging and holding said cylindrical spring housing, said barrel means including slots and a groove sized and positioned within an interior of said barrel means to receive said extending tabs of said cylindrical spring housing and said cylindrical spring housing having a second sealing means to provide an air tight seal between said exterior of said cylindrical spring housing and said interior of said barrel means, said interior of said barrel means shaped sufficient to engage said cylindrical spring housing and allow said resilient legs to flex radially outward; and
(e) a plunger sized to be received concentrically within said barrel means, said plunger having a hollow axially located chamber therein, and having a frangible end and outwardly tapered shoulders adjacent to said frangible end, wherein said frangible end dissociates from said plunger and is ejected into said chamber when said outward tapered shoulders forcibly engage said inwardly tapered shoulders of said hooks of said resilient legs, spreading said resilient legs outwardly and disengaging said hooks from said raised lip of said injection needle, thereby allowing said frangible end to dissociate under a predetermined normal force between said holder of said injection needle and said frangible end, and allowing said coiled spring means to eject said injection needle from said cylindrical spring housing into said chamber within said plunger.

16. A hypodermic syringe system comprising:
(a) a syringe barrel having an attachment end;
(b) a syringe plunger including a frangible end sealing an interior cavity, said syringe plunger sized to be received within and slide through said syringe barrel;
(c) an injection needle; and
(d) a spring holding means including a spring, said spring holding means associated with and held by said syringe barrel, for holding said injection needle and selectively retracting said injection needle into said interior cavity of said syringe plunger when said syringe plunger abuts against and moves beyond a portion of said syringe barrel, causing breakage of said frangible end, and allowing said frangible end of said syringe plunger to separate, and wherein said spring holding means can easily be attached and removed to and from said barrel means.

* * * * *